Figure 1:
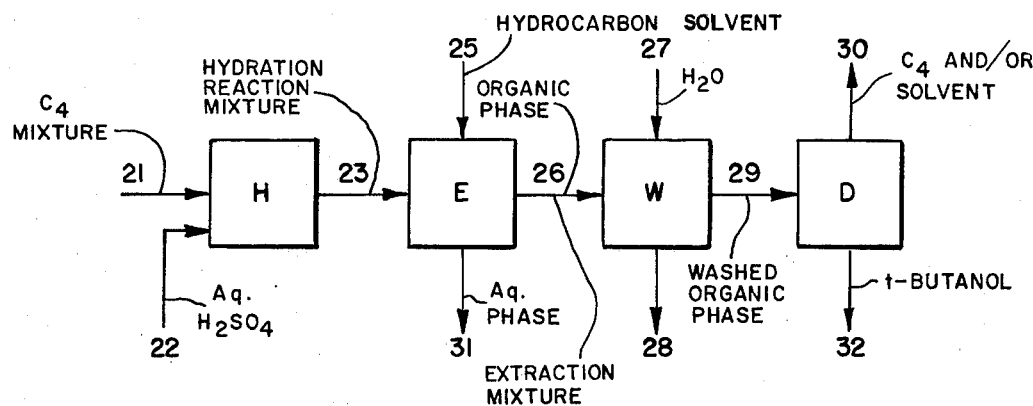

United States Patent [19]
Vogel et al.

[11] 3,950,442
[45] Apr. 13, 1976

[54] MANUFACTURE OF t-BUTANOL

[75] Inventors: Hans-Henning Vogel; Hans-Martin Weitz; Toni Pfeiffer, all of Frankenthal, Germany

[73] Assignee: BASF Aktiengesellschaft, Ludwigshafen (Rhine), Germany

[22] Filed: June 13, 1975

[21] Appl. No.: 586,540

Related U.S. Application Data
[63] Continuation of Ser. No. 409,274, Oct. 24, 1973, abandoned.

[30] Foreign Application Priority Data
Oct. 27, 1972 Germany............................ 2252685

[52] U.S. Cl................................. 260/641; 260/682
[51] Int. Cl.$^2$......................................... C07C 29/06
[58] Field of Search..................................... 260/641

[56] References Cited
UNITED STATES PATENTS
2,042,212  5/1936  Deanesly............................ 260/641
2,221,955  11/1940  Schneider........................... 260/641

*Primary Examiner*—Joseph E. Evans
*Attorney, Agent, or Firm*—Johnston, Keil, Thompson & Shurtleff

[57] ABSTRACT

Process for the manufacture of t-butanol by hydration of isobutylene by reaction of isobutylene or isobutylene-containing $C_4$-hydrocarbon mixtures at moderately elevated temperature with aqueous sulfuric acid and isolation of the t-butanol from the resulting solution of t-butanol in water and sulfuric acid, wherein the reaction is carried out at temperatures of from 20° to 45°C using 20–48% w/w aqueous sulfuric acid, the t-butanol being separated from the t-butanol solution in water and sulfuric acid by extraction, at temperatures of from 0° to 50°C, with saturated or mono-olefinically or di-olefinically unsaturated aliphatic or cycloaliphatic hydrocarbons containing at least 3 carbon atoms or with aromatic hydrocarbons of from 6 to 10 carbon atoms or with a mixture of said hydrocarbons, whereupon the t-butanol is isolated from the extracted mixture of t-butanol and hydrocarbon or hydrocarbon mixture.

3 Claims, 2 Drawing Figures

MANUFACTURE OF T-BUTANOL

This is a continuation of application Ser. No. 409,274, filed Oct. 24, 1973, now abandoned.

This invention relates to a process for the manufacture of t-butanol by hydration of isobutylene with the use of aqueous sulfuric acid.

German Published Application 1,910,473 discloses a process for manufacturing t-butanol by hydration of isobutylene at moderately elevated temperatures by reaction with not more than 50% aqeuous sulfuric acid and separation of the t-butanol formed from the resulting solution of t-butanol in water and sulfuric acid by vacuum distillation, e.g. as an azeotrope with 12% of water. This process has the drawback that the resulting t-butanol contains at least 12% of water. To avoid dissociation of the t-butanol in the sulfuric acid solution it is necessary to use a good vacuum when separating the t-butanol from the solution thereof in aqueous sulfuric acid by distillation, and this makes the process relatively expensive.

It is an object of the invention to provide a process for the manufacture of t-butanol by hydration of isobutylene to produce a virtually anhydrous t-butanol of high purity and in very good yield.

In accordance with the present invention these and other objects and advantages are achieved in a process for the manufacture of t-butanol by hydration of isobutylene by reaction of isobutylene or isobutylene-containing $C_4$-hydrocarbon mixtures at moderately elevated temperature with aqueous sulfuric acid and isolation of the t-butanol from the resulting solution of t-butanol in water and sulfuric acid, wherein the reaction is carried out at temperatures of from 20° to 45°C using 20–48% w/w aqueous sulfuric acid, the t-butanol solution in water and sulfuric acid by extraction, at temperatures of from 0° to 50°C, with saturated or monoolefinically or di-olefinically unsaturated aliphatic or cycloaliphatic hydrocarbons containing at least 3 carbon atoms or with aromatic hydrocarbons of from 6 to 10 carbon atoms or with a mixture of said hydrocarbons, whereupon the t-butanol is isolated from the extracted mixture of t-butanol and hydrocarbon or hydrocarbon mixture.

It is surprising that t-butanol can be obtained in high yield by our novel process, since Belgian Pat. No. 685,666 (cf. Example) states that when isobutylene is reacted with 50% aqueous sulfuric acid at 49°C followed by extraction of the resulting reaction mixture with aliphatic hydrocarbons, e.g. propane, the compound extracted is isobutylene and not t-butanol. It was therefore not foreseeable that the extraction proposed by the present invention causes separation not of isobutylene but of t-butanol, which, as is well known, is miscible with water in all proportions, and that this compound may be isolated in a virtually anhydrous form. The extraction carried out in the process of the invention involves virtually no dissociation of the t-butanol formed to produce isobutylene.

The starting material for the hydration of the invention may be isobutylene itself, but it is particularly advantageous to use the $C_4$-hydrocarbon mixtures obtained in the various dehydrogenation and cracking processes and containing isobutylene, as starting material for the present hydration. When such isobutylene-containing $C_4$-hydrocarbon mixtures are used in the process of the invention, the isobutylene is hydrated in a highly selective manner and with excellent yields. The butenes and butadiene-1,3 contained in the $C_4$-hydrocarbon mixtures react only in traces to form s-butanol and buten-1-ol. Also suitable as starting material is a $C_4$-hydrocarbon mixture also containing small amounts, e.g. less than 5% by weight, of butadiene-1,2, propadiene, propyne or triply unsaturated $C_4$ hydrocarbons.

The hydration of the isobutylene is carried out at temperatures of from 20° to 45°C and preferably from 25° to 40°C. Hydration is effected with a 20–48% and preferably 25–45% and more preferably 35–45% w/w aqueous sulfuric acid solution. It is particularly advantageous to carry out hydration in the presence of aqueous sulfuric acid of the above concentration and already containing additional t-butanol, since this improves the solubility of the isobutylene or the isobutylene-containing $C_4$-hydrocarbon mixture used as starting material so that the rate of hydration of the isobutylene is increased. If such aqueous sulfuric acid containing additional t-butanol is used for hydration, the content of t-butanol and aqueous sulfuric acid is conveniently from 5 to 45% and preferably from 10 to 35% by weight.

Hydration of the isobutylene may be carried out at atmospheric pressure but it is convenient to operate at slightly elevated pressure, e.g. at from 0.01 to 20 and in particular from 1 to 10 atmospheres gage. The isobutylene or isobutylene-containing $C_4$-hydrocarbon mixture may be contacted with the aqueous sulfuric acid either in the form of a liquid or in the gaseous form depending on the pressure and temperature used for the reaction. It is advantageous to contact liquid isobutylene or liquid isobutylene containing $C_4$-hydrocarbon mixture with the aqueous sulfuric acid used in the process of the invention.

It is an important feature of the present invention that the t-butanol obtained by hydration of isobutylene is separated from the resulting aqueous sulfuric acid t-butanol solution by extraction with saturated or mono- or di-olefinically unsaturated aliphatic or cycloaliphatic hydrocarbons of at least 3 carbon atoms or with aromatic hydrocarbons of from 6 to 10 carbon atoms or mixtures of said hydrocarbons. In general, aliphatic or cycloaliphatic hydrocarbons of from 3 to 16 and preferably from 3 to 12 and more preferably from 3 to 8 carbon atoms are used. In the case of aromatic hydrocarbons we prefer to use those having from 6 to 8 carbon atoms. Suitable saturated or mono- or di-olefinically unsaturated aliphatic or cycloaliphatic hydrocarbons are for example propane, butanes, pentanes, hexanes, heptanes, propylene, n-butenes, n-pentenes, n-hexenes, n-heptenes, cyclopentane, cyclohexane, butadiene, isoprene and gasoline fractions. Suitable aromatic hydrocarbons are for example benzene, toluene, xylene and ethylbenzene. It is particularly advantageous to effect extraction with hydrocarbons having 4 carbon atoms or $C_4$-hydrocarbon mixtures. In particular, where isobutylene-containing $C_4$-hydrocarbons are used as starting material, it is convenient to use the virtually isobutylene-free $C_4$-hydrocarbon mixture (raffinate) obtained after hydration of the isobutylene, as the extracting agent.

Di-olefinically unsaturated aliphatic or cycloaliphatic hydrocarbons having conjugated double bonds, such as butadiene or isoprene, may be used as such as extracting agents, but these di-olefinically unsaturated aliphilic or cycloaliphatic hydrocarbons having conjugated double bonds are generally used in admixture with saturated or mono-olefinically unsaturated aliphatic or cycloaliphatic hydrocarbons. An example of such a mixture is a butadiene-containing $C_4$-hydrocarbon mixture obtained from a cracking process and from which any isobutylene has been separated, e.g. by the hydration of the invention.

Extraction is carried out at temperatures of 0° to 50°C and preferably from 10° to 45°C and more preferably from 20° to 40°C. For practical reasons, hydration and extraction are advantageously carried out at the same temperature. Extraction may be effected at atmospheric pressure but it is convenient to operate at slightly elevated pressures, e.g. at from 0.01 to 20 and in particular at from 1 to 10 atmospheres gage.

In the hydration and extraction processes it is desirable to ensure that the various components are thoroughly mixed. Suitable equipment for such vigorous mixing includes for example mixing pumps, pulsed columns equipped for example with sieve plates or packings, and high-speed stirrers. Alternatively, thorough mixing of the components may be effected with the use of nozzles. Hydration and extraction may be carried out in one or more stages. In the case of multistage hydration, use is made of a number of hydrating zones and separating zones for separating the unreacted isobutylene leaving each hydrating zone and in multi-stage extraction use is made of mixing and separating zones arranged alternately. Multi-stage hydration and/or extraction may be suitably carried out by the mixer-settler principle (cf. Kirk-Othmer, Encyclopedia of Chemical Technology, 2nd Ed., Vol. 8, p. 743). In multi-stage work it is convenient to cause the components involved in the hydration and extraction to flow countercurrently to each other. However, it is possible to operate with a cocurrent of said components.

When the starting material is an isobutylene-containing $C_4$-hydrocarbon mixture, it is possible to use the essentially isobutylene-free $C_4$-hydrocarbons leaving the hydrating stage as the extracting agent. Alternatively, the hydrocarbons or hydrocarbon mixture proposed in the present invention may be added to said isobutylene-free $C_4$-hydrocarbons mixture for the purpose of extraction. The process of the invention may be carried out batchwise or, preferably, continuously. In continuous operation, the sulfuric acid leaving the extraction unit with a reduced content of t-butanol is generally recycled to the hydration unit, which recycled sulfuric acid desirably has a content of t-butanol of from 5 to 40% and preferably from 10 to 35% and more preferably from 10 to 25%, by weight of the mixture of t-butanol and aqueous sulfuric acid. Since water is consumed in the hydration, it is necessary, in continuous operation, to add water to the recycled sulfuric acid in order to maintain the concentration of sulfuric acid required in the hydration by the present invention.

Isolation of the t-butanol from the mixture of t-butanol and hydrocarbon(s) (extract) obtained on extraction is carried out in known manner, for example by distillation. When isolating the t-butanol by distillation it is convenient to remove traces of sulfuric acid from the extract prior to distillation, for example by washing the extract with an appropriate amount of water or caustic soda in, say, a column. Distillation of the extract may be carried out at, say, atmospheric pressure or alternatively at elevated pressure. When distillation is carried out at superatmospheric pressure, it is particularly necessary to remove the sulfuric acid as far as possible from the extract by washing, in order to avoid acid-catalyzed dissociation of the t-butanol during distillation.

FIG. 1 is a flow chart of an example of one embodiment of the process of the invention. In the hydration zone H, the isobutylene or isobutylene-containing $C_4$-hydrocarbon mixture 21 is vigorously mixed with aqueous sulfuric acid 22 optionally containing t-butanol. t-Butanol is then extracted from the mixture 23 leaving the hydration zone, this extraction taking place in the extraction zone E using the hydrocarbon or hydrocarbon mixture 25 proposed for such extraction by the present invention. The sulfuric acid 31 leaving the extraction zone with a reduced content of t-butanol may be recycled to the hydration zone H. When the t-butanol is isolated from the extract by distillation, the extract 26 is conveniently washed with water 27 in the washer W. In general, the amount of water used in such water washing is the same as that which has been consumed in the hydration of the isobutylene. The small amounts of sulfuric acid and t-butanol 28 separated in the washer W may be recycled to the hydration zone or, advantageously, to the extraction zone. The washed extract 29 is separated in the distillation zone D to give t-butanol 32 as bottoms and the said hydrocarbon or hydrocarbon mixture as overheads 30, which may then be recycled to the extraction zone E.

Dehydration of the t-butanol obtained in the process of the invention provides a very pure isobutylene which is particularly suitable for the manufacture of high molecular weight polymers of isobutylene.

EXAMPLE 1

Figure 2:
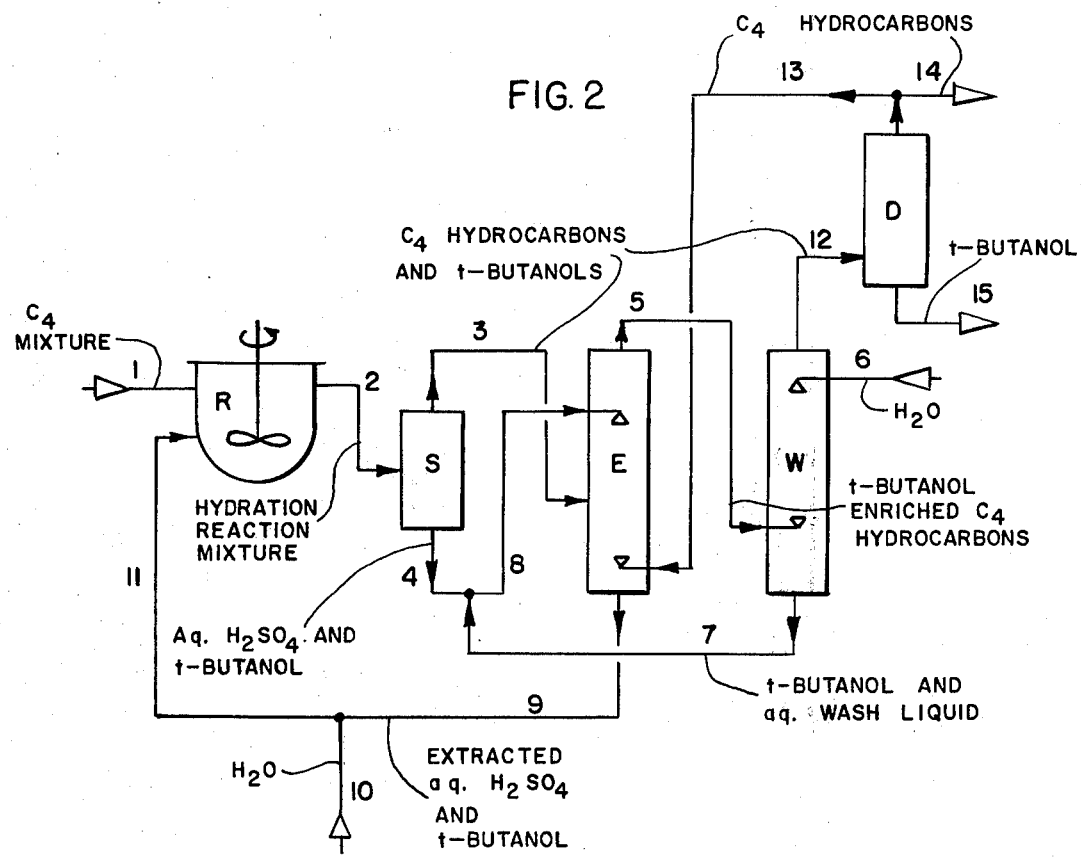

Using equipment as represented in FIG. 2, a butadiene-free $C_4$-hydrocarbon mixture 1 containing 48% by weight of isobutylene is contacted with a mixture of 80% w/w of 41% w/w aqueous sulfuric acid and 20% w/w of t-butanol in a stirred autoclave R at 35°C and a total pressure of 5 atmospheres absolute. The resulting reaction mixture 2 passes continuously from the stirred autoclave R to the separating vessel S. From the separating vessel S, the upper layer 3 consisting of virtually isobutylene-free $C_4$-hydrocarbons and t-butanol dissolved therein and the lower layer of aqueous sulfuric acid containing 28.8% by weight of t-butanol are passed to the extraction column E, where they are contacted with liquid $C_4$-hydrocarbon mixture 13 countercurrently for extraction of the t-butanol. The bottoms from the extraction column E consist of a t-butanol/aqueous sulfuric acid mixture 9 having a reduced content of t-butanol and may be recycled to the autoclave R through line 11, if necessary after adding water through line 10.

The overheads 5 from the extraction column E consist of a mixture of $C_4$-hydrocarbon mixture and t-butanol and this is washed countercurrently in the washer W to remove small amounts of sulfuric acid, the amount of water 6 used being the same as that consumed in the hydration of the isobutylene. The bottoms 7 from the washer W consist of a mixture of t-butanol, sulfuric acid and water and this is added to the mixture of sulfuric acid and t-butanol leaving the separating vessel S and is thus recycled to the extraction column E via line 8. The overheads 12 of the washer W consist of a sulfuric acid-free mixture of t-butanol and $C_4$-hydrocarbons which is then distilled in the distilling column D. The overheads of the distilling column D comprise an isobutylene-free $C_4$-hydrocarbon mixture, of which a partial stream 13 is recycled to the extraction column E. The raffinate stream 14 is a virtually isobutylene-free C₄ hydrocarbon mixture containing 4.06% of isobutylene. The bottoms 15 of the distilling column D are t-butanol having a purity of more than 99.8%. The amounts and compositions of the main streams are given in the following Table:

between the phases at a point above the packing. The organic phase is removed at the top of the column at a rate of 97.1 g/hr. The organic phase contains 11.8% by weight of t-butanol which has been extracted from the sulfuric acid phase by the C₄-hydrocarbons. The bottoms of the column consist of 1,232.9 g/hr of t-butanol-containing aqueous sulfuric acid, this mixture contain-

TABLE 1

| | 1 | 2 | 3 | 4 | 5 | 6+10 | 7 | 8 | 9 | 10 | 11 | 12 | 13 | 14 | 15 |
|---|---|---|---|---|---|---|---|---|---|---|---|---|---|---|---|
| isobutene | 0,48 | 0,022 | 0,002 | — | 0,064 | — | — | — | — | — | — | 0,064 | 0,042 | 0,022 | — |
| butadiene | — | — | — | — | — | — | — | — | — | — | — | — | — | — | — |
| butane/butenes | 0,52 | 0,58 | 0,520 | 0,60 | 1,532 | — | — | 0,06 | 0,06 | — | 0,06 | 1,532 | 1,012 | 0,520 | |
| t-butanol | — | 1,402 | 0,172 | 1,230 | 0,625 | — | 0,020 | 1,250 | 0,797 | — | 0,797 | 0,605 | — | — | 0,605 |
| H₂SO₄ | — | 1,307 | 0,025 | 1,282 | 0,025 | — | 0,025 | 1,307 | 1,307 | — | 1,307 | — | — | — | — |
| H₂O | — | 1,734 | 0,025 | 1,709 | 0,025 | 0,147 | 0,172 | 1,881 | 1,881 | — | 1,881 | — | — | — | — |
| s-butanol | | | | | | | | | | | | | | | |
| buten-1-ol-3 | | | | | | | | | | | | | | | |
| diisobutene | | | | | | | | | | | | | | | |
| | 1,00 | 5,045 | 0,764 | 4,281 | 2,271 | 0,147 | 0,217 | 4,498 | 4,045 | — | 4,045 | 2,201 | 1,054 | 0,542 | 0,605 |

From the amount of t-butanol obtained (stream 15, 0.605 kg/hr), a yield of 94.5% of theory is calculated based on the isobutylene used. The amount of diisobutylene formed is less than 0.3% of the isobutylene introduced.

EXAMPLE 2

Example 1 is repeated except that a C₄-hydrocarbon mixture of the following composition is used:

| | % w/w |
|---|---|
| isobutylene | 30.8 |
| butadiene-1,3 | 44.3 |
| cis-butene-2 | 1.0 |
| trans-butene-2 | 3.2 |
| butene-1 | 14.6 |
| n-butane | 5.6 |
| isobutane | 0.5 |
| | 100.0 |

The yield of t-butanol is 93.8% based on the isobutylene used. The t-butanol obtained contains less than 0.05% by weight of buten-1-ol-3. In the raffinate obtained by distillation, there are less than 4% by weight of isobutylene. Catalytic dehydration of the t-butanol obtained over aluminum oxide gives an isobutylene having a butadiene content of less than 350 ppm by weight.

EXAMPLE 3

Example 2 is repeated except that a mixture of 45% w/w aqueous sulfuric acid and t-butanol is used in which the content of t-butanol is 20% by weight. The t-butanol produced contains less than 0.2% by weight of buten-1-ol-3.

EXAMPLE 4

In a pulsed column having an internal diameter of 25 mm and a height of 2 m and packed with glass rings having a diameter of 5 mm, a C₄-hydrocarbon mixture is passed at a rate of 280 g/hr and at a pressure of 4 atmospheres gage countercurrently to 1,150 g/hr of a 5:1 mixture of 41% w/w aqueous sulfuric acid and t-butanol, the temperature being from 30° to 35°C. The residence time of the C₄-hydrocarbon mixture in the column is approximately 15–30 minutes. The input and output are controlled so as to maintain the boundary ing 26.3% by weight of t-butanol and from 1 to 2% by weight of dissolved C₄-hydrocarbons. The organic phase is distilled after venting to atmospheric pressure, the raffinate consisting of 83.2 g/hr of C₄-hydrocarbon mixture and the bottoms comprising 11.5 g/hr of t-butanol. The composition of the C₄-mixture used and of the raffinate is given in Table 2 below.

TABLE 2

| | Starting C₄-mixture | Raffinate |
|---|---|---|
| butadiene-1,3 | 0.10% | 0.18% |
| cis-butene-2 | 6.47% | 11.66% |
| trans-butene-2 | 9.88% | 17.81% |
| isobutylene | 46.67% | 3.89% |
| butene-1 | 25.90% | 46.69% |
| n-butane | 9.08% | 16.35% |
| isobutane | 1.90% | 3.42% |
| Total | 100.00% | 100.00% |

The bottoms of the packed column consisting of t-butanol-containing aqueous sulfuric acid are used in the recovery of further t-butanol in a manner similar to that described in Example 5 below using a pulsed packed column at 35°C and a pressure of 4 atmospheres gage, where they are extracted with a virtually isobutylene-free C₄-hydrocarbon mixture passed countercurrently thereto.

EXAMPLE 5

3,581 g of a mixture of t-butanol and 40% w/w sulfuric acid, the content of t-butanol in said mixture being 30% by weight, are passed countercurrently to 948 g of a C₄-hydrocarbon mixture of the composition given in column I of Table 3 below in a pulsed packed column such as described in Example 4 over 5 hours and at a pressure of 4 atmospheres gage and a temperature of 35°C. The bottoms of the column consist of 3,280.3 g of t-butanol-containing aqueous sulfuric acid containing 22.7% by weight of t-butanol and from 1 to 3% by weight of C₄-hydrocarbons. The overheads of the packed column consist of 1,248.7 g of an organic phase containing 25.8% by weight of t-butanol and 1.58% by weight of sulfuric and also 1.74% by weight of water. The organic phase is vented, diluted with water and then distilled at atmospheric pressure. The overheads obtained in this distillation consist of 885 g of C₄-hydrocarbon mixture having the composition given in column II of Table 3. The bottoms obtained in said distillation contain 322.2 g of t-butanol.

TABLE 3

|  | I | II |
|---|---|---|
| butene-1 | 39.54 | 39.32 |
| cis-butene-2 | 15.93 | 15.84 |
| trans-butene-2 | 24.18 | 24.03 |
| isobutene | 3.06 | 3.59 |
| n-butane | 15.29 | 15.24 |
| isobutane | 1.62 | 1.61 |
| butadiene-1,3 | 0.39 | 0.37 |

EXAMPLE 6

In a pulsed packed column of the kind described in Example 4, 2,815 g of a mixture of 2,015.5 g of 43% w/w aqueous sulfuric acid and 799.5 g (28.4% by weight) of t-butanol, as obtained by hydration according to the present invention, are extracted, over 4 hours and at a pressure of 4 atm. gage and a temperature of 45°C, with 704 g of a $C_4$-mixture having the composition given in column I of Table 4 below.

TABLE 4

|  | I | II |
|---|---|---|
| butene-1 | 39.34 | 38.96 |
| cis-butene-2 | 15.93 | 15.78 |
| trans-butene-2 | 24.11 | 23.87 |
| isobutene | 3.40 | 4.35 |
| n-butene | 15.22 | 15.07 |
| isobutane | 1.62 | 1.60 |
| butadiene-1,3 | 0.38 | 0.37 |

The bottoms of the column consist of 2,614.8 g of aqueous sulfuric acid containing 22.5% by weight of t-butanol. The overheads of the column consist of 949.9 g of an organic phase containing 1.3% by weight of sulfuric acid, 1.5% by weight of water and 22.3% by weight of t-butanol. The organic phase is then vented and distilled at atmospheric pressure as described in example 4 to remove the $C_4$-hydrocarbons. The distillate obtained consists of 711 g of $C_4$ cut having the composition given in column II of Table 4 above. The residue consists of 212.2 g of t-butanol. The composition of the $C_4$-mixture given in column II of Table 4 above shows that only 1.15% by weight of the t-butanol present in the feed to the column is dehydrated to isobutylene under these conditions.

EXAMPLE 7

As described in Example 4, the isobutylene is hydrated in a $C_4$-mixture containing isobutylene and butadiene-1,3. To this end, 4,936 g of a 5:1 mixture of 40% w/w aqueous sulfuric acid and t-butanol is contacted countercurrently with 680 g of a $C_4$-hydrocarbon mixture over 4 hours. The $C_4$-mixture has the composition given in column I of Table 5 below. The overheads consist of 524.2 g of organic phase, which contains 1.5% by weight of sulfuric acid, 1.8% by weight of water and 14.0% by weight of t-butanol. The organic phase is vented and condensed in a cold trap. The raffinate obtained from the condensed organic phase as the overheads of the distilling column has the composition given in column II of Table 5 below.

TABLE 5

|  | I | II |
|---|---|---|
| butadiene-1,3 | 44.3 | 60.77 |

TABLE 5-continued

|  | I | II |
|---|---|---|
| cis-butene-2 | 1.0 | 1.37 |
| trans-butene-2 | 3.2 | 4.39 |
| isobutene | 30.8 | 5.07 |
| butene-1 | 14.6 | 20.03 |
| n-butane | 5.6 | 7.68 |
| isobutane | 0.5 | 0.68 |

The bottoms obtained from the distillation consist of t-butanol containing less than 0.03% by weight of buten-1-ol-3 and less than 0.2% by weight of diisobutylene. The bottoms of the extracting column consist of 5,091.8 g of aqueous t-butanol-containing sulfuric acid having a content of 22.9% by weight of t-butanol. From this t-butanol-containing aqueous sulfuric acid, further amounts of t-butanol are isolated by extraction in a manner similar to that described in Example 5.

EXAMPLE 8

Example 7 is repeated except that a 45% w/w aqueous sulfuric acid is used. The raffinate thus contains only 3.2% by weight of isobutylene. The t-butanol obtained contains 0.05% by weight of buten-1-ol-3 and less than 0.4% by weight of diisobutylene.

EXAMPLE 9

In a pulsed packed column, 3,125 g of a mixture of 43% w/w aqeuous sulfuric acid containing 30% by weight of t-butanol, obtained as described in Example 4, are extracted countercurrently, over 4 hours at a temperature of from 40° to 45°C and a pressure of 4 atm. gage, with 680 g of n-pentane. The organic phase is withdrawn from the top of the column in an amount of 760 g. The organic phase contains 15.10% by weight of t-butanol, 0.80% by weight of sulfuric acid and 0.95% by weight of water. The bottoms of the column consist of 3,055.9 g of aqueous sulfuric acid containing 26.9% by weight of t-butanol and 1.9% by weight of n-pentane. The organic phase is vented and distilled to give n-pentane containing less than 0.8% by weight of isobutylene.

EXAMPLE 10

In a pulsed packed column, 3,008 g of a mixture of 43% w/w aqueous sulfuric acid containing 30% by weight of t-butanol, obtained as described in Example 4, are extracted, over 4 hours at a temperature of 35°–40°C and a pressure of 4 atm. gage, with a countercurrent of 722 g of n-heptane. The organic phase is removed from the top of the column in an amount of 747.5 g. This organic phase contains 0.83% by weight of t-butanol, 0.94% by weight of sulfuric acid, 1.12% by weight of water and less than 0.7% by weight of isobutylene. The bottoms of the column consist of 2,982.5 g of aqueous sulfuric acid containing 27.8% by weight of t-butanol and 2.05% by weight of n-heptane.

EXAMPLE 11

In a pulsed packed column, 2,902 g of a mixture of 43% w/w aqueous sulfuric acid containing 30% by weight of t-butanol obtained as described in Example 4 are extracted, over 4 hours at a temperature of from 35° to 40°C and a pressure of 4 atm. gage, with a counter-current of 754 g of benzene. The organic phase is removed from the top of the column in an amount of 866.1 g. This organic phase contains 15.1% of t- butanol, 1.14% of sulfuric acid, 1.20% of water and less than 0.6% of isobutylene, by weight. The bottoms of the column consist of 2,789.9 g of aqueous sulfuric acid containing 26.3% by weight of t-butanol and 1.58% by weight of benzene.

We claim:

1. A process for the manufacture of t-butanol by hydration of isobutylene comprising
    a. contacting in a hydrating stage an isobutylene-containing $C_4$-hydrocarbon mixture at temperatures of 20° to 45°C and at a pressure from 1 to 10 atmospheres gauge with a mixture of aqueous sulfuric acid and t-butanol, the concentration of the aqueous sulfuric acid being 25 to 45% w/w at the beginning of the reaction and the concentration of the t-butanol in the mixture of aqueous sulfuric acid and t-butanol being from 10 to 35% w/w at the beginning of the reaction,
    b. passing the mixture obtained in the hydrating stage to a separation stage to obtain an essentially isobutylene-free and t-butanol containing $C_4$-hydrocarbon mixture and a t-butanol/aqueous sulfuric acid mixture,
    c. introducing the essentially isobutylene-free and t-butanol containing $C_4$-hydrocarbon mixture and the t-butanol/aqueous sulfuric acid mixture of step (b) at separate points into an extraction stage and adding essentially isobutylene-free and t-butanol-free $C_4$-hydrocarbon mixture to the extraction stage to obtain an extracted mixture of t-butanol and $C_4$-hydrocarbon and a t-butanol/aqueous sulfuric acid mixture having a reduced content of t-butanol, said extraction stage being at 0° to 50°C, and
    d. recycling the t-butanol/aqueous sulfuric acid mixture having a reduced content of t-butanol to the hydrating stage and isolating the t-butanol from the extracted mixture of t-butanol and $C_4$-hydrocarbon mixture.

2. A process as claimed in claim 1 wherein step (a) is carried out at temperatures of 25° to 40°C.

3. A process as claimed in claim 1 wherein the hydration and the extraction are carried out at the same temperature.

* * * * *